(12) United States Patent
Ellis

(10) Patent No.: US 7,667,547 B2
(45) Date of Patent: Feb. 23, 2010

(54) LOOSELY-COUPLED OSCILLATOR

(75) Inventor: Michael G. Ellis, Alpharetta, GA (US)

(73) Assignee: CardioMEMS, Inc., Atlanta, GA (US)

( * ) Notice: Subject to any disclaimer, the term of this patent is extended or adjusted under 35 U.S.C. 154(b) by 167 days.

(21) Appl. No.: 11/843,101

(22) Filed: Aug. 22, 2007

(65) Prior Publication Data

US 2009/0051445 A1    Feb. 26, 2009

(51) Int. Cl.
*H03L 7/00* (2006.01)
(52) U.S. Cl. .......................... 331/16; 331/65
(58) Field of Classification Search ............ 331/16, 331/65; 324/71.1
See application file for complete search history.

(56) References Cited

U.S. PATENT DOCUMENTS

| | | | |
|---|---|---|---|
| 4,265,252 A | | 5/1981 | Chubbuck et al. |
| 5,218,343 A | * | 6/1993 | Stobbe et al. ............ 340/573.4 |
| 5,264,809 A | * | 11/1993 | Tamino ..................... 331/65 |
| 5,581,248 A | * | 12/1996 | Spillman et al. ......... 340/870.31 |
| 6,015,386 A | * | 1/2000 | Kensey et al. ............... 600/486 |
| 6,111,520 A | * | 8/2000 | Allen et al. .............. 340/870.16 |
| 6,206,835 B1 | * | 3/2001 | Spillman et al. ............ 600/485 |
| 6,650,227 B1 | * | 11/2003 | Bradin ....................... 340/10.3 |
| 6,855,115 B2 | | 2/2005 | Fonseca et al. |
| 7,147,604 B1 | | 12/2006 | Allen et al. |
| 7,298,361 B2 | * | 11/2007 | Lin et al. ..................... 345/163 |
| 2003/0136417 A1 | | 7/2003 | Fonseca et al. |
| 2005/0187482 A1 | | 8/2005 | O'Brien et al. |
| 2006/0196277 A1 | | 9/2006 | Allen et al. |
| 2007/0096715 A1 | | 5/2007 | Joy et al. |
| 2008/0077016 A1 | * | 3/2008 | Sparks et al. ............... 600/459 |

FOREIGN PATENT DOCUMENTS

| | | |
|---|---|---|
| EP | 0942281 A | 9/1999 |
| WO | 2006/060226 A | 6/2006 |

OTHER PUBLICATIONS

PCT International Search Report and Written Opinion—PCT/US2007/019050, Nov. 5, 2008.

\* cited by examiner

*Primary Examiner*—Joseph Chang
*Assistant Examiner*—Jeffrey Shin
(74) *Attorney, Agent, or Firm*—Kilpatrick Stockton LLP

(57) ABSTRACT

Certain embodiments of the present invention provide a loosely-coupled oscillator including a circuit and an electronic device that are not physically connected. The electronic device may include an amplifier for amplifying a signal to produce an output signal and include a wire connected to an input of the amplifier. The wire can be electromagnetically coupled to the circuit that is physically disconnected from the electronic device. The output signal can be produced at an output of the amplifier without transmitting an excitation signal from the electronic device to the circuit and when the wire is electromagnetically coupled to the circuit.

19 Claims, 11 Drawing Sheets

LOOSELY-COUPLED OSCILLATOR

TECHNICAL FIELD

The present invention relates generally to oscillators and specifically to electronic oscillators having at least some components that are not physically connected and are adapted to identify objects or provide information associated with the objects.

BACKGROUND

Electronic oscillators can be used in a variety of applications to provide an oscillating signal at one or more frequencies. For example, oscillators can be used in radio frequency ("RF") transmitting and receiving systems to provide a carrier signal or to demodulate a received signal. An example of a simple electronic oscillator, also known as a tank circuit, includes an inductor connected in parallel to a capacitor and a voltage source. In a tank circuit, the oscillator frequency or resonant frequency (fo) can be determined using the capacitance (C) and inductance (L) with the following relationship:

$$fo = \frac{1}{2\pi\sqrt{LC}}.$$

Other electronic oscillators include a 555 oscillator/timer, Armstrong oscillator, direct digital synthesis oscillator, phase shift oscillator, quartz crystal oscillator, and Resistor/Capacitor (RC) oscillator.

Conventional oscillators often require a drive signal, such as an applied voltage, in order to oscillate. For example, the tank circuit may include an AC voltage source to drive, or cause, the LC circuit to oscillate at its resonant frequency. Typically, the AC voltage source is physically connected to the LC circuit.

Some applications of LC circuits, however, require that the source of the drive signal be disconnected from the LC circuit. In such systems, LC circuits or other oscillators are driven by an electromagnetic signal from a transmitter. An example of such a system is disclosed in U.S. patent application Ser. No. 11/613,645, titled "Communicating with an Implanted Wireless Sensor," filed Dec. 20, 2006. The devices disclosed in U.S. patent application Ser. No. 11/613,645 include a sensor, such as an LC resonant circuit, implanted in a patient and a system for communicating with, and determining the resonant frequency of, the implanted sensor. The system drives the sensor using an RF burst that is an energizing signal, causing the sensor to oscillate at its resonant frequency and emit a sensor signal. The system then receives the sensor signal and determines the resonant frequency of the sensor and associated sensor characteristics.

Although such systems have been successful in obtaining characteristics associated with a sensor, a need exists for an oscillator that does not require an energizing signal to cause a sensor to oscillate or additional electronics to control and process signal transmission and reception. Furthermore, a need exists for an oscillator that includes components that are not physically connected.

SUMMARY OF THE INVENTION

Aspects and embodiments of the present invention provide a loosely-coupled oscillator including a sensor circuit and an electronic device that are not physically connected. When electromagnetically coupled, the sensor circuit and electronic device form an oscillator that is adapted to output an oscillation signal. The resonant frequency of the sensor circuit can be obtained based on the oscillation signal. For example, the oscillation signal may have the same frequency as the resonant frequency.

In one embodiment of the present invention, the sensor circuit includes an inductor and a capacitor and the electronic device includes an amplifier stage and a feedback network. The amplifier stage can include an input and an output and the feedback network can be connected to the input and the output. The input to the amplifier stage may be connected to ground. In some embodiments, the input to the amplifier stage is connected to ground via a wire or a coil. When the electronic device is brought in proximity to the sensor circuit, such as by moving the electronic device until the coil is close to, but not physically touching, the sensor circuit, the impedance of the input to the amplifier stage increases and produces an oscillation signal at the output of the amplifier stage.

These embodiments are mentioned not to limit or define the invention, but to provide examples of embodiments of the invention to aid understanding thereof. Embodiments are discussed in the Detailed Description, and further description of the invention is provided there. Advantages offered by the various embodiments of the present invention may be further understood by examining this specification.

BRIEF DESCRIPTION OF THE DRAWINGS

These and other features, aspects, and advantages of the present invention are better understood when the following Detailed Description is read with reference to the accompanying drawings, wherein.

DETAILED DESCRIPTION

Certain embodiments of the present invention provide a loosely-coupled oscillator having at least two components that are not physically connected. The oscillator may include a sensor circuit and an electronic device that are not physically connected. When the sensor circuit and electronic device are electromagnetically connected, an oscillation signal is produced at the electronic device output. The oscillation signal may be used to determine a resonant frequency of the sensor circuit. In some embodiments, the sensor circuit is adapted to be attached, implanted, or otherwise associated with an object. Various characteristics or properties about the object in which the sensor circuit is associated can be determined from the resonant frequency of the sensor circuit.

Figure 1:
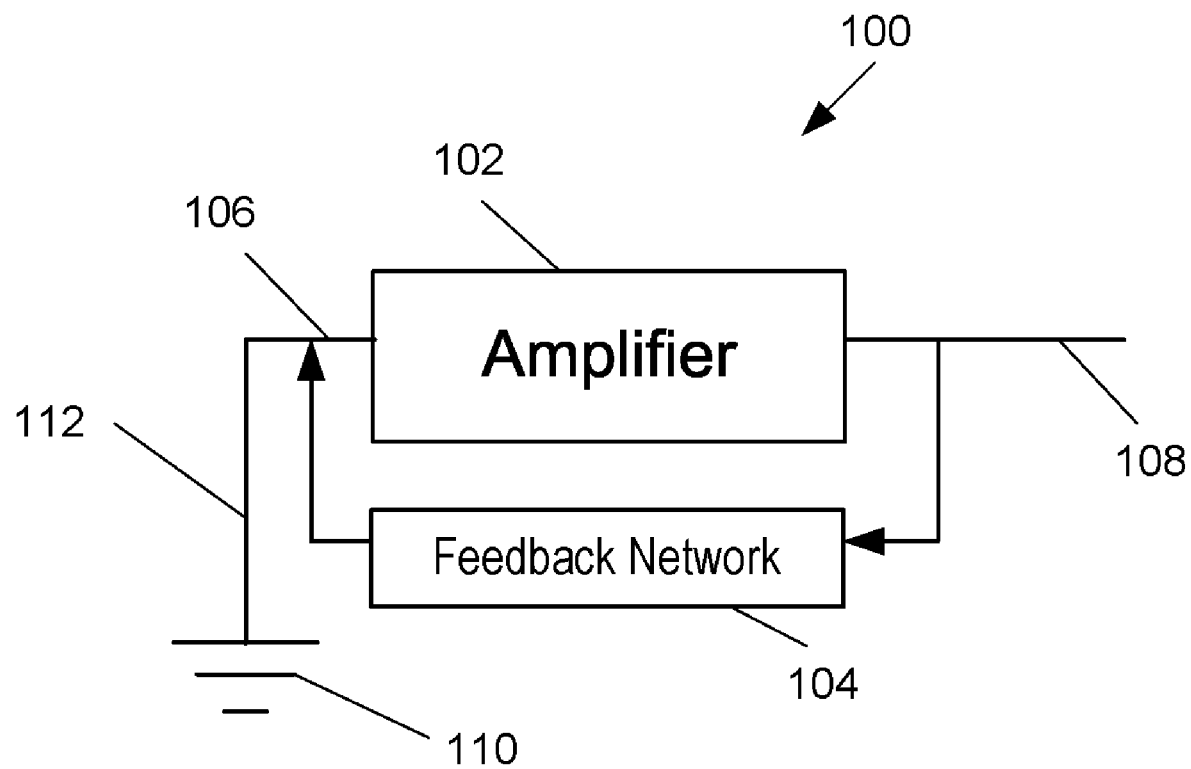
FIG. 1 is a block diagram of an electronic device according to one embodiment of the present invention.

FIG. 1 illustrates one embodiment of an electronic device 100. The electronic device 100 can include an amplifier stage 102 and a feedback network 104. The amplifier stage 102 can include an input 106 and an output 108. The feedback network 104 can be connected to the input 106 and the output 108 of the amplifier stage 102 to provide a feedback loop. The input 106 can also be connected to an electrical ground 110 via a wire 112 or some other electrically conducting material or structure. For example, the wire 112 may be a coil having a diameter at a predetermined size. As discussed in more detail below, a voltage source may be connected to the amplifier stage 102 to provide the amplifier stage 102 with the ability to amplify any input signal. When the input 106 is connected to electrical ground 110, energy from the feedback network 104 that allows the amplifier stage 102 to amplify an input signal is shorted to electrical ground 110 and the electronic device 100 does not output an oscillation signal.

Figure 2:
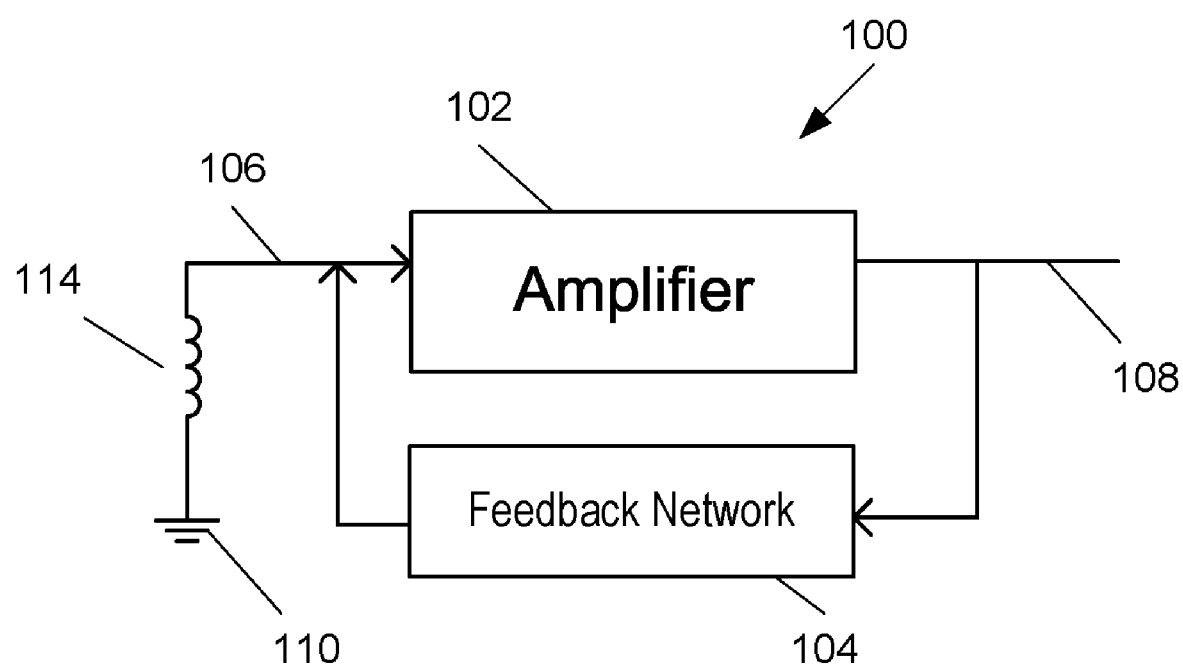
FIG. 2 is a block diagram of an electrically equivalent electronic device to the electronic device of FIG. 1.
Figure 3:
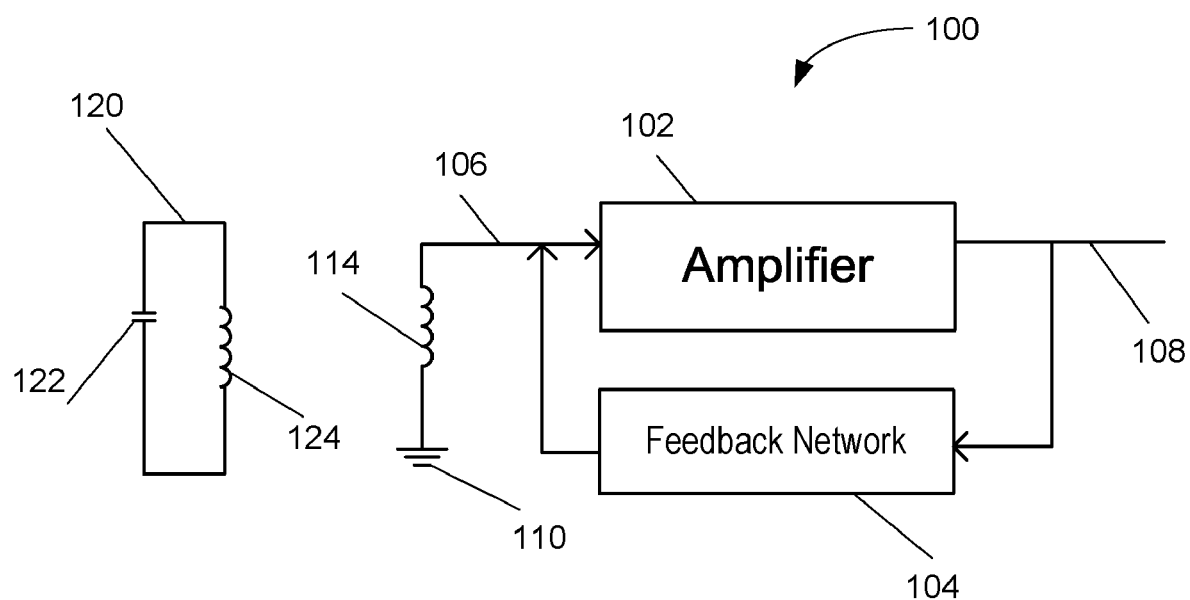
FIG. 3 is a block diagram of a loosely-coupled oscillator according to one embodiment of the present invention.

The wire 112 may have a small inductance and can be represented as an inductor. FIG. 2 illustrates the electronic device 100 with the wire 112 replaced with its electrical equivalent, inductor 114. Without an input signal or other excitation energy input signal, however, the inductor 114 shorts the input to the amplifier stage 102 to electrical ground 110 and an oscillation signal is not provided at the output 108. In FIG. 3, the electronic device 100 is brought in proximity to a sensor circuit 120. The sensor circuit 120 can include a capacitor 122 and an inductor 124, but may include any circuitry components that have a resonant frequency and are adapted to form an oscillator with the electronic device 100.

One example of a sensor circuit that may be used in some embodiments of the present invention is described in U.S. patent application Ser. No. 11/157,375, titled "Implantable Wireless Sensor For In Vivo Pressure Measurement," filed Jun. 21, 2005. The described sensor includes a body formed from electrically insulating materials, such as fused silica. The body includes a lower chamber and an upper chamber and deflectable region at the lower end of the body. An LC resonator that includes a capacitor and an inductor is housed within the body. The capacitor, which may be located in the lower chamber, includes at least two plates, a lower capacitor plate and an upper capacitor plate, disposed in parallel and spaced apart in relation. The inductor includes a coil located in the upper chamber that is in conductive electrical contact with the capacitor. The lower capacitor plate is positioned on the inner surface of the deflectable region of the sensor body. The upper capacitor plate is positioned on a fixed region of the sensor body. A change in ambient pressure at the deflectable region of the sensor causes the deflectable region to bend and displace the lower capacitor plate with respect to the upper capacitor plate. The displacement causes the capacitance and the resonant frequency of the LC sensor to change.

Examples of other sensors that may be used in certain embodiments of the present invention are also disclosed in the following: U.S. patent application Ser. No. 10/943,772, titled "Implantable Wireless Sensor," filed Sep. 16, 2004; U.S. patent application Ser. No. 10/054,671, titled "Implantable Wireless Sensor," filed Jan. 22, 2002; U.S. Pat. No. 6,855,115, titled "Implantable Wireless Sensor For Pressure Measurement Within The Heart," filed Jan. 22, 2002; and U.S. Pat. No. 7,147,604, titled "High Q Factor Sensor," filed Aug. 7, 2002.

In some embodiments, the sensor circuit 120 can include at least two LC circuits. The at least two LC circuits may contain different circuitry and have different resonant frequencies. The inductor 124 may be a coil or electrically conducting wire having a predetermined diameter.

When the electronic device 100 is brought in proximity to the sensor circuit 120, electromagnetic coupling between the electronic device 100 and sensor circuit 120 causes the electronic device 100 to sense the presence of the sensor circuit 120. For example, the sensor circuit inductor 124 may be magnetically or inductively coupled to the electronic device inductor 114. As the electronic device 100 is brought closer to the sensor circuit 120, electromagnetic coupling causes the impedance of the electronic device inductor 114 to increase. The impedance of the electronic device inductor 114 may continue to increase at the resonant frequency of the sensor circuit 120 until it reaches a level in which the feedback in the electronic device 100 is no longer shorted to ground and an output signal is provided by the electronic device at the resonant frequency of the sensor circuit 120. As the impedance increases, an input signal is provided from the feedback network 104 at the amplifier stage input 106, amplified by the amplifier stage 102, and provided at the output 108. The frequency of the input signal corresponds to the resonant frequency of the sensor circuit 120. In some embodiments, the frequency of the input signal may be the same as the resonant frequency of the sensor circuit 120 and the output signal is an amplified signal at the resonant frequency.

Figure 4:
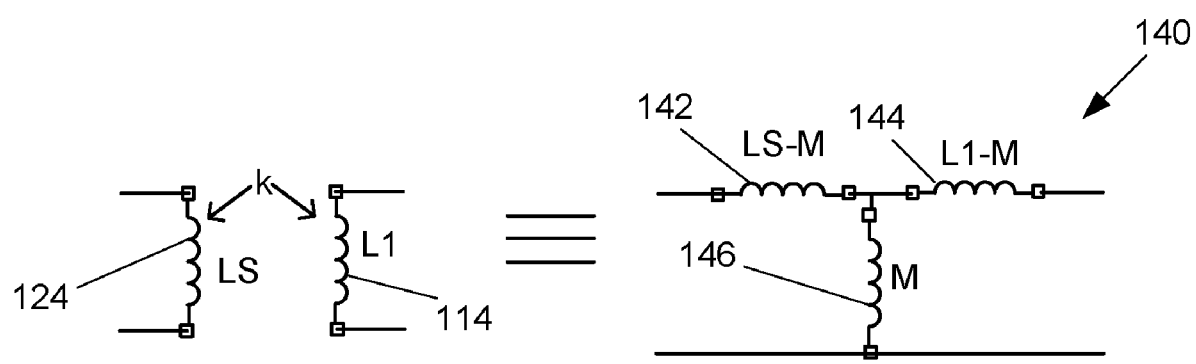
FIG. 4 shows the physical equivalent of a sensor circuit electromagnetically coupled to an electronic device input according to one embodiment of the present invention.

The electromagnetic coupling of the sensor circuit inductor 124 and electronic device inductor 114 may be the same as using a mutual inductance between inductors 114, 124. FIG. 4 shows one embodiment of sensor circuit inductor LS 124 and electronic device coil inductor L1 114 and their electrical equivalent circuit 140 during electromagnetic coupling. The electrical equivalent circuit 140 includes an equivalent sensor circuit inductor Ls-M 142, an equivalent electronic device inductor L1-M 144, and a mutual inductor M 146. The mutual inductor M 146 can be connected to a common node of both the equivalent sensor circuit inductor Ls-M 142 and equivalent electronic device inductor L1-M 144.

Figure 5:
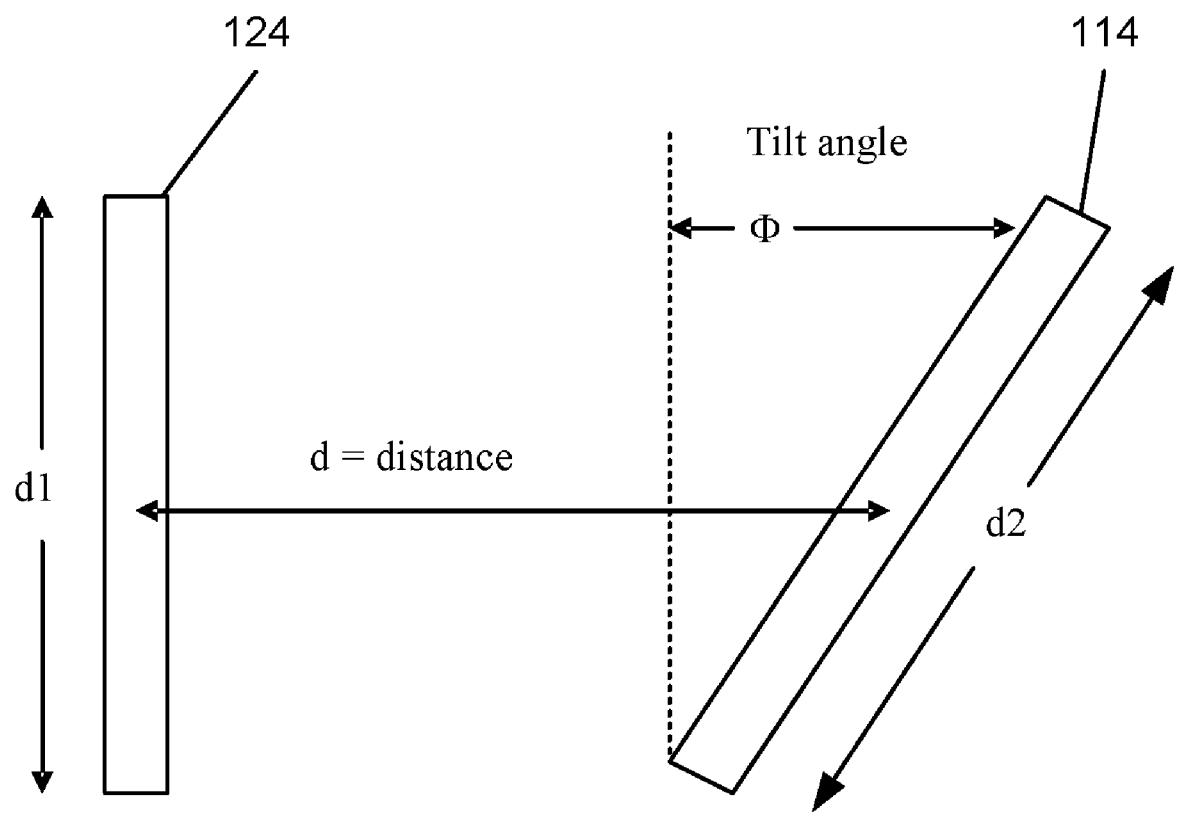
FIG. 5 shows a geometrical configuration of a sensor circuit electromagnetically coupled to an electronic device input according to one embodiment of the present invention.

The inductance, M, of the mutual inductor M 146 can be determined based on a coefficient of coupling, k, and the inductance, Ls, L1, of the sensor circuit inductor 124 and electronic device inductor 114, respectively, using the following relationship: $M=k\sqrt{Ls*L1}$. The coefficient of coupling, k, can be determined using physical parameters of inductors 114, 124. FIG. 5 shows one embodiment of physical parameters of sensor inductor Ls 124 and electronic device inductor L1 114 that may be used to determine the coefficient of coupling between inductor Ls 124 and inductor L1 114. FIG. 5 shows the sensor circuit inductor Ls 124 having a diameter, d1, and the electronic device inductor L1 114, which may be a coil, having a diameter, d2. By dividing each of d1 and d2 by 2, a radius, r1 and r2, can be determined for the sensor circuit inductor Ls 124 and electronic device inductor L1 114, respectively. A distance, d, between the sensor circuit inductor Ls 124 and electronic device inductor L1 114 can be obtained. The distance, d, can be measured from the center of the sensor circuit inductor Ls 124 and electronic device inductor L1 114. A tilt angle, $\Phi$, of the electronic device inductor L1 114 relative to a vertical position can be obtained.

Using these physical parameters, the coefficient of coupling, k, can be obtained by the following relationship:

$$k = \frac{(r1)^2 * (r2)^2 * \cos(\Phi)}{\sqrt{r1 * r2} * [(r2)^2 + d^2]^{3/2}},$$

where r1 is the radius of the sensor circuit inductor Ls 124, r2 is the radius of the electronic device inductor L1 114, d is the distance between the inductors 114, 124, and Φ is the tilt angle relative to a vertical position of the electronic device inductor L1 114. After determining the mutual inductance M, the electrical equivalent circuit may be provided to an electronic circuit analysis software program and simulated to allow the user to select a value for sensor circuit inductor 124 and configure the size and shape of the coil to provide the selected inductance value.

Furthermore, the mutual inductance, M, can reflect changes that might occur to both inductors 114, 124. For example, as the electronic device 100 in FIG. 3 is brought close to sensor circuit 120, the resonant frequency of the sensor circuit 120 may be changed by the impedance of the inductor 124 being affected by inductor 114 and the impedance of inductor 114 may be affected based on the presence of the sensor circuit 120. In some embodiments of the present invention, the inductor 114 is connected to an amplifier having a high input impedance and a feedback network having a high impedance at the node that the inductor 114 is connected. The high impedance can decrease or prevent the presence of inductor 114 from affecting the resonant frequency of the sensor circuit 120 and the presence of the sensor circuit 120 from affecting inductor 114.

Figure 6:
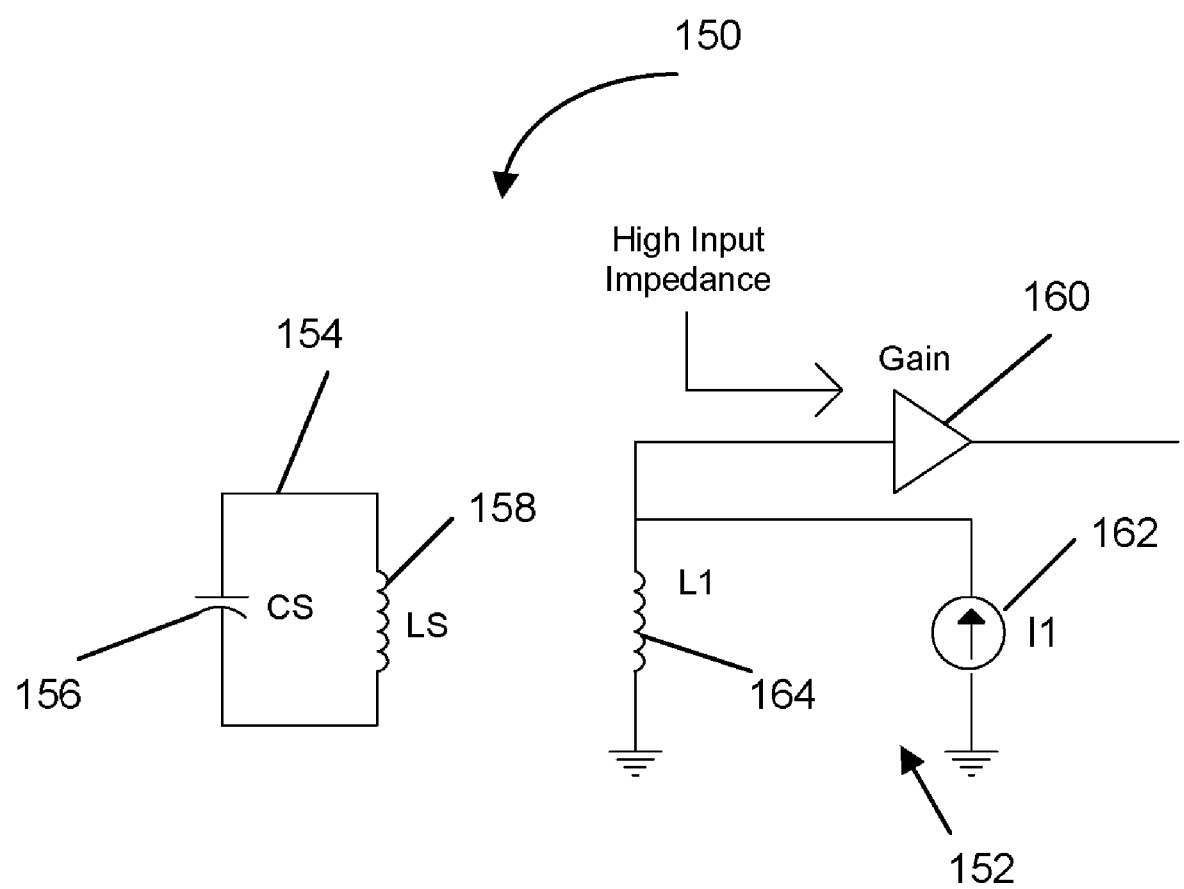
FIG. 6 is a schematic of a loosely-coupled oscillator according to one embodiment of the present invention.

FIG. 6 schematically shows an oscillator 150 according to one embodiment of the present invention. The oscillator 150 includes an electronic device 152 and sensor circuit 154. The sensor circuit 154 is an LC circuit, including a capacitor 156 and an inductor 158, that is adapted to resonate at a resonant frequency. The electronic device 152 includes an amplifier stage and a feedback stage. The amplifier stage includes a gain 160 and amplifies an input signal and provides an output voltage. The feedback stage includes a current source I1 162. The current source I1 162 includes a current that is proportional to the output voltage of the gain 160 that provides a high impedance at the amplifier stage input. The input of the amplifier stage may also have a high input impedance due to the input to gain 160 and be connected to ground via a coil. The coil may have an inductance, such as inductor L1 164.

An input signal can be obtained at the input of the amplifier stage when the electronic device 152 is brought in proximity to the sensor circuit 154. By terminating the coil into a high impedance, the resonant frequency of the sensor circuit 154 can be obtained without a shift of the resonant frequency that may be caused by the distance between the electronic device 152 and sensor circuit 154.

In some embodiments of the present invention, an electronic device may be provided with an amplifier stage having a low input impedance and a feedback network providing a low input impedance. A sensor circuit may also be provided that has a resonant frequency. The resonant frequency of the sensor circuit may be known. As the electronic device is brought in proximity to a sensor circuit, an input signal may be obtained at the amplifier stage. The inductance of the electronic device coil may affect the resonant frequency of the sensor circuit, based on the distance between the electronic device and the sensor circuit. An output signal is obtained and its frequency measured. The frequency difference between the output signal and the resonant frequency of the sensor circuit can be obtained. Based on the frequency difference, the distance between the electronic device and the sensor circuit can be determined and used to locate the sensor circuit.

Figure 7:
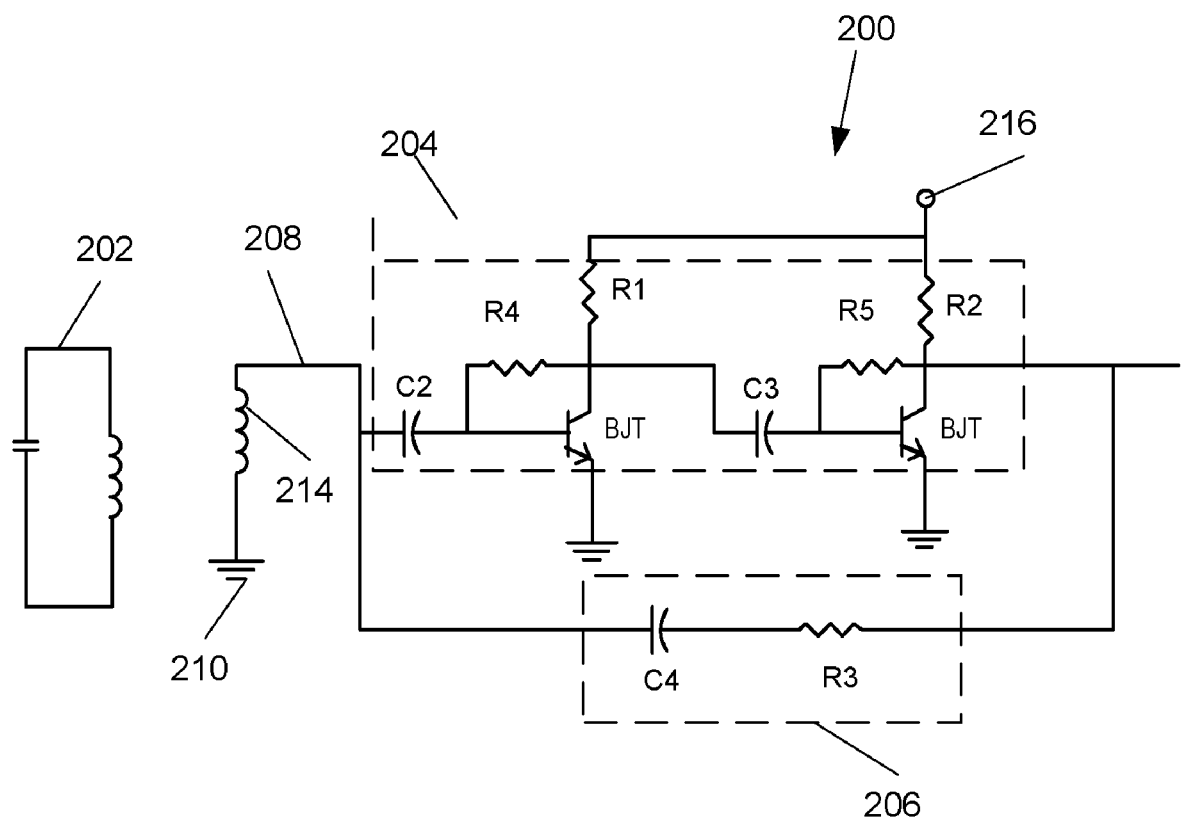
FIG. 7 is a schematic of a loosely-coupled oscillator using a bi-polar junction transistor according to one embodiment of the present invention.

FIGS. 7-10 schematically show an oscillator according to certain embodiments of the present invention. In FIG. 7, an electronic device 200 and sensor circuit 202 are shown. The electronic device 200 includes an amplifier stage 204 that uses circuitry, such as bipolar transistor junction (BJT) transistors to amplify an input signal, a feedback network 206, and a coil connected to electrical ground 210 and the input of the amplifier stage 204. The coil may be represented as electronic device inductor 214. The electronic device 200 may also be connected to a voltage source 216 that provides the amplifier stage 204 with the ability to amplify the input signal. The sensor circuit 202 can include an LC network. In some embodiments, the sensor circuit 202 includes several LC networks, each having a distinct resonant frequency. The sensor circuit 202 may include any circuitry components adapted to form an oscillator with the electronic device 200. Certain embodiments of the sensor circuit 202 may be adapted to be implanted or otherwise installed into an object.

When the electronic device 200 is brought in proximity to the sensor circuit 202, electromagnetic coupling causes the impedance of inductor 214 to increase. As the impedance of inductor 214 increases, signals are no longer shorted to ground and an input signal is supplied to the input of the amplifier stage 204. The input signal may have a frequency that is the same as, or different than, the resonant frequency of the sensor circuit 202. The amplifier stage 204 can amplify the input signal and provide an output signal having the same frequency of the input signal. The output signal can be measured to determine the resonant frequency of the sensor circuit 202. Based on the resonant frequency of the sensor circuit 202, characteristics associated with the object in which it is implanted, or the position of the sensor circuit 202 relative to the electronic device 200, can be determined.

Characteristics associated with the object can be determined by comparing the measured resonant frequency with stored information in a database. For example, the sensor circuit 202 may be implanted into a living body, such as a human body. The living body may apply pressure or temperature to the sensor circuit 202 and change its resonant frequency. If a baseline sensor circuit resonant frequency is known, such as by measuring the resonant frequency of the sensor circuit 202 before implanting it into the living body or just after implanting it into the living body, the measured resonant frequency can be compared to the baseline resonant frequency to determine the changes occurring to the implanted sensor circuit 202 and associate them to changes occurring in the living body. Another example of using the measured resonant frequency to determine characteristics associated with an object, is implanting or installing the sensor circuit 202 into a device, product, product packaging, or otherwise some type of non-living object. A resonant frequency of the sensor circuit 202 can be obtained and associated with an identification of the object in a database. The sensor circuit 202 components can be manufactured to prevent the resonant frequency of the sensor circuit 202 from changing or changing by more than a pre-set amount. At a later time, the resonant frequency can be measured and compared to the database to identify the object without requiring the user to visually identify the object or otherwise use other forms of identification, such as barcode scanners.

Figure 8:
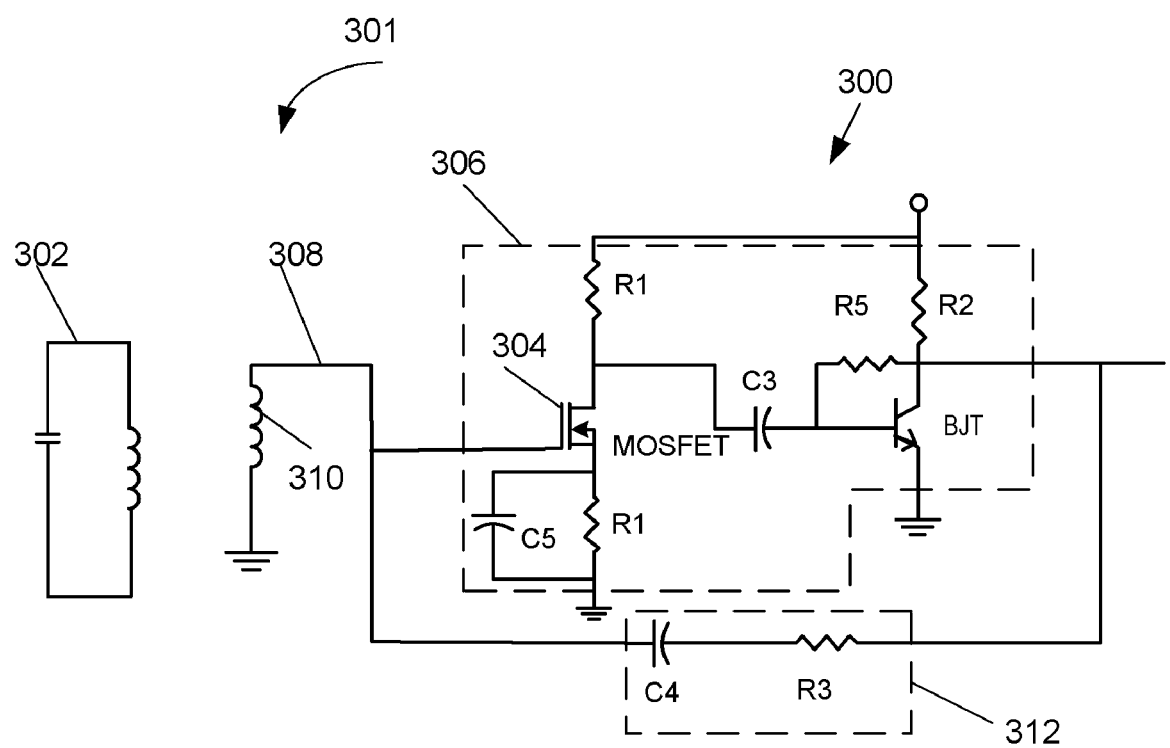
FIG. 8 is a schematic of a loosely-coupled oscillator using a MOSFET transistor according to one embodiment of the present invention.

FIG. 8 schematically shows an oscillator 301 that includes an electronic device 300 and a sensor circuit 302, where the electronic device 300 includes circuitry, such as at least one field effect transistor, MOSFET transistor 304, in an amplifier stage 306. The MOSFET transistor 304 can include a higher impedance than a BJT. Using a MOSFET transistor 304 at the input of the amplifier stage 306 can reduce the effect the electronic device coil 308 that is electrically equivalent to inductor 310, has on the resonant frequency of the sensor circuit 302.

Figure 9:
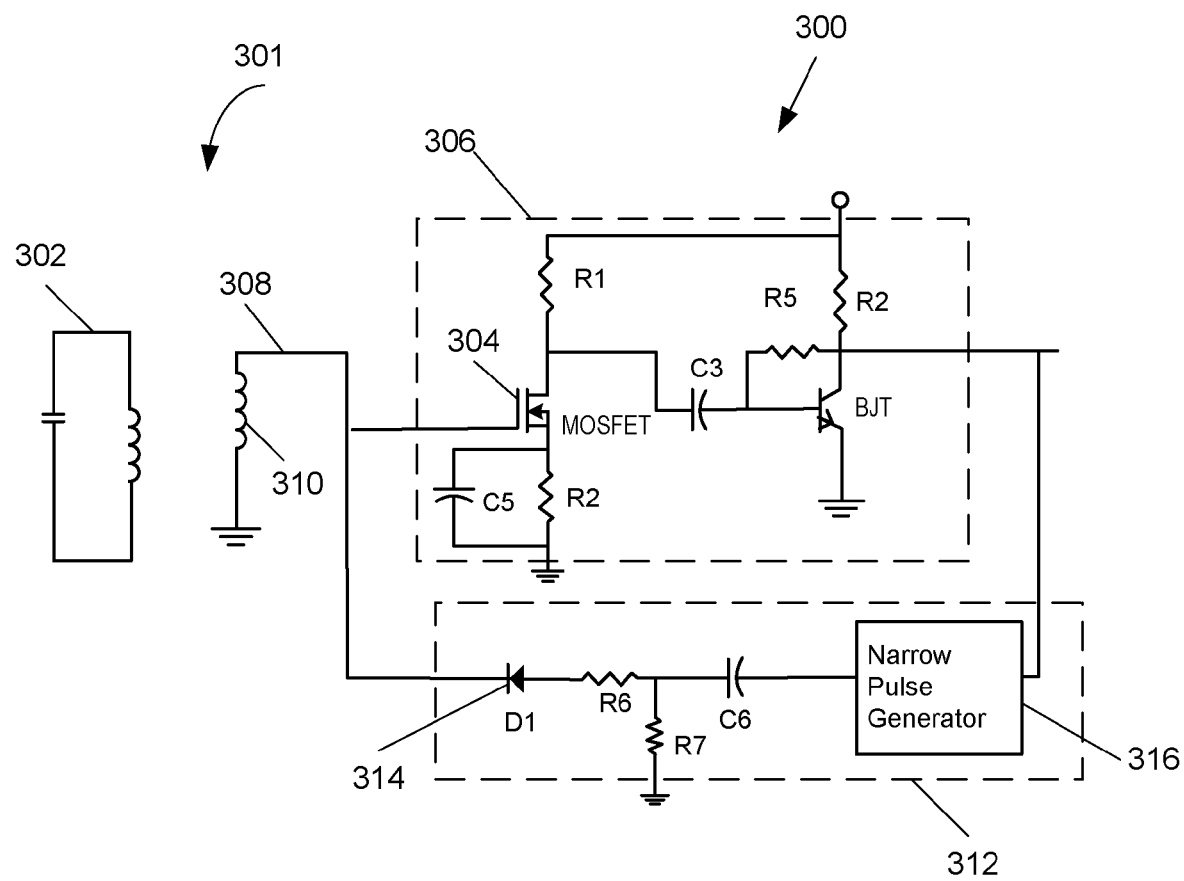
FIG. 9 is a schematic of a loosely-coupled oscillator that includes a narrow pulse generator according to one embodiment of the present invention.

The electronic device 300, however, also includes a feedback network 312 that includes circuitry having a low impedance that may allow the electronic device coil 308 to affect the resonant frequency of the sensor circuit 302. Additional circuitry components may be included in an electronic device feedback network to reduce or eliminate the effect the electronic device coil 308 has on the sensor circuit 302. For example, as shown in FIG. 9, a diode 314 and narrow pulse generator 316 may be added to the feedback network 312 and provide a high impedance to the feedback network 312. The narrow pulse generator 316 provides a pulse to turn on, bias, or otherwise activate the diode 314 to allow signals to pass towards the input of the amplifier stage 306. In some embodiments, the narrow pulse generator 316 provides a pulse for 1 µs for every 1 ms. The effect that the electronic device coil 308 has on the resonant frequency of the sensor circuit 302 is reduced or otherwise eliminated using the amplifier stage 306 with a high input impedance and a feedback network with a high impedance.

Figure 10:
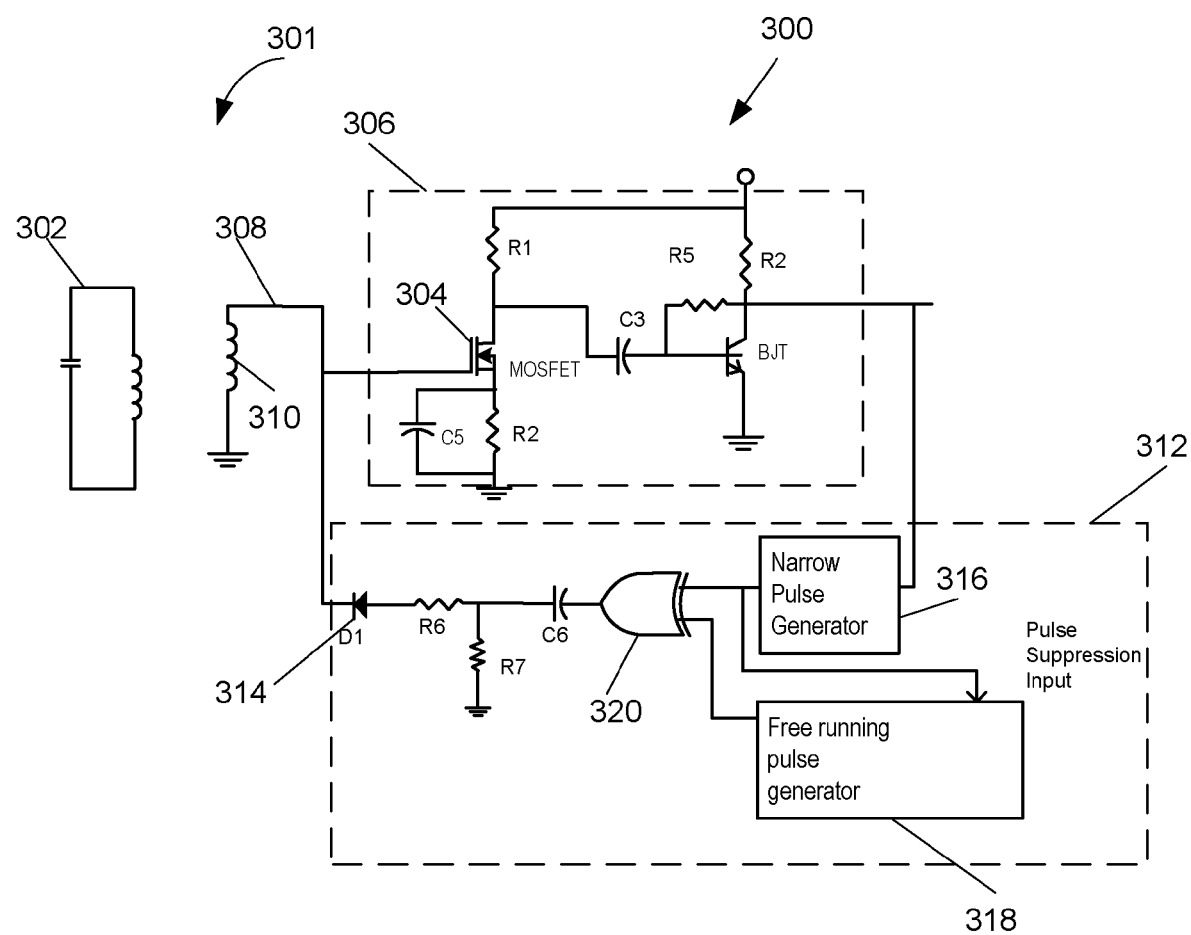
FIG. 10 is a schematic of a loosely-coupled oscillator that includes a free running pulse generator according to one embodiment of the present invention.
Figure 11A:
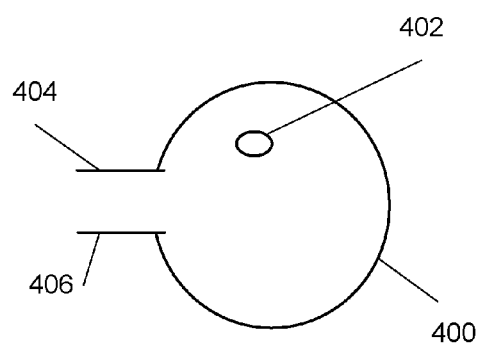
FIGS. 11A-D are physical views of a sensor circuit and electronic device coil according to one embodiment of the present invention.
Figure 11B:
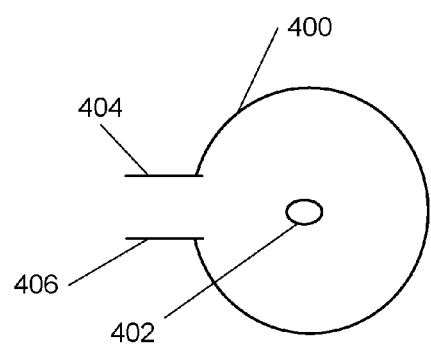
Figure 11C:
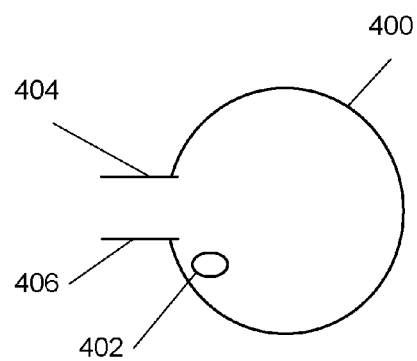
Figure 11D:
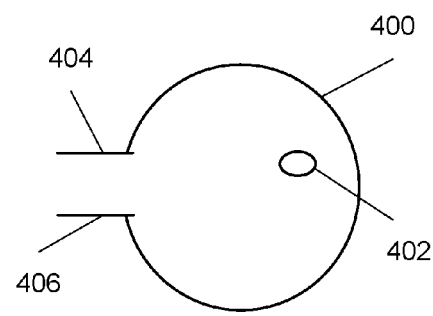

In some embodiments, the additional components included in FIG. 9 may not allow the oscillator 301 to oscillate without an external stimulation signal applied to the feedback network 312. FIG. 10 shows one embodiment of additional components that provide a stimulation signal to the feedback network 312. The additional components include a free running pulse generator 318 and an "Or" gate 320. The free running pulse generator 318 can provide a pulse to "kick-start" or otherwise allow the oscillator 301 to begin oscillating upon bringing the electronic device 300 in proximity to the sensor circuit 304. Once the oscillator begins oscillating, the output oscillation signal is fed to the narrow pulse generator 316 and causes it to begin generating a pulse signal in accordance with the description with reference to FIG. 9. When the narrow pulse generator 316 begins providing a signal, it can output a command to the free running pulse generator 318 to stop providing its signal. The "Or" gate 320 can be configured to logically allow the signals from the free running pulse generator 318 to pass if no signal is provided from the narrow pulse generator 316 or allow signals from the narrow pulse generator 316 to pass when the free running pulse generator 318 stops passing signals.

As described above, embodiments of the present invention may be used for a variety of purposes to determine characteristics or otherwise identify objects with which they are implanted, inserted, or otherwise associated with. The electronic device may include a wire, such as a coil, that is used to electromagnetically couple the electronic device with the sensor circuit. FIGS. 11A-D show embodiments of using a coil 400 to electromagnetically couple an electronic device (not shown) to a sensor circuit 402. The coil 400 may be a wire in an essentially circular shape with at least two lead wires 404, 406 and form the electrical equivalent of an inductor. One lead wire 404 may be connected to electrical ground, while a second lead wire 406 can be connected to the electronic device amplifier stage and feedback network. As shown in FIGS. 11A-D, the sensor circuit 402 may be anywhere within the diameter of the coil 400. The resonant frequency of the sensor circuit 402 is the same, no matter its location within the coil diameter since the coefficient of coupling, k, is the same.

In one embodiment of the present invention, the sensor circuit 402, such as an LC circuit having a resonant frequency, is implanted just under a person's skin. The resonant frequency of the sensor circuit 402 may be any frequency in the range of 100 kHz to 200 MHz. The inductor coil of the sensor circuit 402 is between 1 millimeter and 2.5 millimeters in diameter. A baseline resonant frequency of the sensor circuit 402 may be obtained before or just after implantation and saved into a database. The sensor circuit 402 may be configured to change characteristics based on pressure and/or temperature experienced in its implanted environment, such as inside the person's body. At a time after obtaining the baseline resonant frequency, a measured resonant frequency can be obtained by moving the electronic device in proximity to the sensor circuit 402, such as by placing the coil 400 close to or on top of the skin in the area that the sensor circuit 402 is implanted. Coil 400 may have a diameter of between 1 millimeter and 2.5 millimeters and may have the same diameter as the inductor coil of the sensor circuit 402. Electromagnetic coupling causes the electronic device to oscillate and provide an oscillation signal at an output that is the same frequency of the resonant frequency. The measured resonant frequency can be compared to the baseline frequency and changes between the two resonant frequencies can be obtained. Characteristics associated with the person can be obtained based on these changes.

In another embodiment of the present invention, the sensor circuit 402 can be attached, implanted, or otherwise associated with a living or non-living object to provide identification functionality or obtain characteristics associated with the object. The sensor circuit 402 can include an inductor having a diameter between 1 millimeter and 100 millimeters. The coil 400 of the electronic device may have the same diameter as the sensor circuit inductor. The resonant frequency of the sensor circuit 402 can be obtained before or after being associated with the object. The resonant frequency can be mapped to a description that identifies the object and this mapped relationship can be stored in a database. At a later time, the electronic device can be brought in proximity to the sensor circuit 402 that is associated with the object. For example, the electronic device may be moved until the coil 400 is adjacent to the skin where the sensor circuit is implanted. In some embodiments of the present invention, the electronic device is in proximity to the sensor circuit 402 if it is between a few millimeters to several centimeters from the sensor circuit 402. The distance between the coil 400 and sensor circuit 402 may be dependent on the physical configuration of the coil 400 and/or the sensor circuit 402, such as the size of the coil 400 and the inductor coil of the sensor circuit 402, and the level of accuracy with which the resonant frequency of the sensor circuit 402 must be measured. When the coil 400 is brought in sufficient proximity to the sensor circuit 402, the electronic device can output an oscillation signal having a frequency that corresponds to the resonant frequency of the sensor circuit 402. The oscillation signal frequency can be compared to the database to locate an entry describing the same frequency and the object can be identified using the mapped identification information associated with that frequency.

In another embodiment of the present invention, the sensor circuit 402 may be associated with an object and the electronic device may be located in a fixed position at a predetermined distance from the object. The object may be adapted to rotate, such as a tire on a car, a fan, or some other object that moves in a rotatable fashion. As the object rotates, the sensor circuit 402 is periodically located in proximity to the coil 400 and the electronic device can sense the sensor circuit 402 and output a signal burst at the resonant frequency of the sensor circuit 402. The periodic occurrence of the signal burst can be obtained and used to determine characteristics of the object. For example, the periodic occurrence of the signal burst can be used to determine to speed of a rotating tire on a car or otherwise.

The examples described above are provided for illustrative purposes only. The present invention should not be limited to those examples described. Different and/or additional applications of various embodiments of the present invention are possible. The foregoing description of the embodiments of the invention has been presented only for the purpose of illustration and description and is not intended to be exhaustive or to limit the invention to the precise forms disclosed. Numerous modifications and adaptations are apparent to those skilled in the art without departing from the spirit and scope of the invention.

What is claimed is:

1. An oscillator comprising:
a sensor circuit comprising an inductor and a capacitor, the sensor circuit being adapted to resonate at a resonant frequency;
an electronic device physically disconnected from the sensor circuit, the electronic device comprising an input and an output, the input being connected to electrical ground through an electronic device coil, the electronic device being adapted to amplify an input signal to produce an output signal at the electronic device output, the electronic device comprising:
an amplifier stage adapted to amplify the input signal, wherein the amplifier stage comprises circuitry adapted to provide a high amplifier stage input impedance to prevent the electronic device coil from changing the resonant frequency of the sensor circuit; and
a feedback network connected to an input of the amplifier and an output of the amplifier stage and adapted to provide a feedback for the amplifier stage, the feedback network comprising a pulse generator configured to provide a start-up pulse and a high impedance for the feedback network at the input of the amplifier stage; and
wherein the sensor circuit and the electronic device are electromagnetically coupled to obtain the input signal at the electronic device input, the output signal having characteristics associated with the resonant frequency of the sensor circuit, the characteristics comprising a frequency that is the same as the resonant frequency.

2. The oscillator of claim 1, wherein the sensor circuit is adapted to be associated with an object.

3. The oscillator of claim 2, wherein the electronic device is adapted to determine characteristics associated with the object using the output signal.

4. An electronic device, comprising:
an amplifier for amplifying a signal to produce an output signal, the amplifier comprising an input and an output; and
a wire connected to the input of the amplifier, the wire configured to be electromagnetically coupled to a circuit that is physically disconnected from the electronic device and that has a resonant frequency, wherein the wire is capable of sensing a presence of the circuit when the wire is located in proximity to the circuit without transmitting an excitation signal from the wire to the circuit,
wherein the output signal is produced at the output of the amplifier when the wire is electromagnetically coupled to the circuit, the output signal having characteristics associated with the resonant frequency of the circuit.

5. The electronic device of claim 4, wherein the wire is a coil coupled to electrical ground.

6. The electronic device of claim 5, wherein an impedance of the coil is configured to increase when the coil is electromagnetically coupled to the circuit.

7. The electronic device of claim 4, wherein the amplifier comprises:
an amplifier stage for amplifying the signal to produce the output signal, the signal being obtained without transmitting an excitation signal from the electronic device to the circuit and when the wire is electromagnetically coupled to the circuit; and
a feedback network for providing a feedback for the amplifier stage, the feedback network being connected to the input of the amplifier and the output of the amplifier.

8. The electronic device of claim 7, wherein the amplifier stage comprises circuitry adapted to provide a high amplifier stage input impedance to prevent the wire from changing a resonant frequency of the circuit.

9. The electronic device of claim 4, wherein the wire is electromagnetically coupled to the circuit when the wire is in proximity to the circuit.

10. The electronic device of claim 4, wherein the output signal comprises a frequency corresponding to a resonant frequency of the circuit.

11. The electronic device of claim 4, wherein the output signal is produced when the wire is electromagnetically coupled to the circuit associated with an object.

12. A method comprising:
sensing a presence of a circuit by a wire by locating the wire in proximity to the circuit and without transmitting an excitation signal from the wire to the circuit, the circuit being physically disconnected from the wire, wherein the circuit has a resonant frequency and the wire is connected to an amplifier input;
producing an input signal at the amplifier input when the impedance of the wire increases as the wire is brought in proximity to the circuit, wherein the input signal is produced without transmitting an excitation signal from the wire to the circuit, and wherein the input signal has characteristics associated with the resonant frequency of the circuit; and
producing an output signal at an amplifier output by amplifying the input signal, the output signal having characteristics associated with the resonant frequency of the circuit.

13. The method of claim 12, further comprising determining the resonant frequency of the circuit using the output signal.

14. The method of claim 13, wherein the circuit is associated with an object, the method further comprising:
determining characteristics of the object using the resonant frequency of the circuit.

15. The method of claim 14, wherein determining characteristics of the object using the resonant frequency of the circuit comprises:
determining a first resonant frequency before the circuit is associated with the object;

determining a frequency of the output signal;
determining a difference between the first resonant frequency and the frequency of the output signal; and
determining the characteristics of the object based on the difference between the first resonant frequency and the frequency of the output signal.

16. The method of claim 12, wherein the wire is a coil.

17. The method of claim 16, wherein the coil is coupled to electrical ground.

18. The method of claim 12, wherein sensing the presence of the circuit by the wire by locating the wire in proximity to the circuit and without using the excitation signal between the wire and the circuit comprises electromagnetically coupling the wire to the circuit.

19. The method of claim 12, further comprising:
providing a start-up pulse to the amplifier input to generate a high impedance at the amplifier input; and
decreasing an effect of the wire on the resonant frequency of the circuit using the high impedance at the amplifier input.

* * * * *